US00PP11519P

United States Patent [19]

Yoshida et al.

[11] Patent Number: Plant 11,519

[45] Date of Patent: Sep. 26, 2000

[54] APPLE TREE NAMED 'JM7'

[75] Inventors: Yoshio Yoshida, Ebetsu; Shichiro Tsuchiya, Ryugasaki; Junichi Soejima, Morioka; Shosuke Sadamori, Nagano-ken; Tadayuki Haniuda, Nagano; Tetsuro Sanada, Morioka; Yoshiki Kashimura, Tsukuba; Tetsuo Masuda, Morioka; Hideo Bessho, Yamanashi-ken; Sadao Komori, Ishigaki; Yuji Ito, Ibaraki-ken, all of Japan

[73] Assignee: National Institute of Fruit Tree Science, Ministry of Agriculture, Forestry and Fisheries, Tsukuba, Japan

[21] Appl. No.: 09/044,179

[22] Filed: Mar. 19, 1998

[51] Int. Cl.[7] ..... A01H 5/00

[52] U.S. Cl. ..... Plt./174

[58] Field of Search ..... Plt./172, 174, 173, Plt./161

[56] References Cited

U.S. PATENT DOCUMENTS

P.P. 3,028 2/1971 Thompson ..... Plt./173

*Primary Examiner*—Howard J. Locker
*Assistant Examiner*—Wendy Anne Baker
*Attorney, Agent, or Firm*—Armstrong, Westerman, Hattori, McLeland & Naughton

[57] ABSTRACT

Disclosed herein is an apple tree which can be used as an apple dwarfing rootstock. The apple tree is capable of reproduction from hardwood cuttings, exhibits excellent disease and insect resistance, particularly against crown rot, Alternaria blotch and wooly apple aphid, has dwarfing capability and graft compatibility, exhibits satisfactory growth and grows to a size usable as a rootstock in one season after cuttings, and is therefore excellent as an apple dwarfing rootstock.

10 Drawing Sheets

BACKGROUND OF THE VARIETY

The present invention relates to a new and distinct variety of apple tree, specifically a dwarfing rootstock variety of apple tree which is capable of reproduction from hardwood cuttings and which exhibits excellent disease and insect resistance, environmental adaptability and graft compatibility.

In Japan, cultivation of dwarfed apple trees to date occupies 23% of the total cultivation area, but many problems remain to be solved. The dwarfing apple rootstocks mainly used in Japan at the present time are 'M.26' (unpatented) and 'M.9' (unpatented), but these M-line dwarfing rootstocks are associated with such problems as outbreak of violet root rot, cankers and crown rot, and weak tree vigor due to development of burrknots. Also, because the M-line rootstocks cannot be propagated by hardwood cuttings in the manner of the traditional 'Maruba Kaido' (*Malus prunifolia* BORKH. var. ringo Asami) (unpatented), it is common in Japan to graft M-line stocks onto 'Maruba Kaido' for use as double stocks. For this reason, extra costs are incurred for nursery stock production, while high growth after planting prevents adequate performance of the characteristics of the dwarfing rootstocks.

It is an object of the present invention to improve these disadvantages of current dwarfing rootstock varieties, and to raise a rootstock variety which is capable of reproduction from hardwood cuttings and which exhibits excellent disease and insect resistance, environmental adaptability, graft compatibility and dwarfing capability.

ORIGIN AND ASEXUAL REPRODUCTION OF THE VARIETY

The new variety of apple tree according to the invention was obtained in 1972 in the form of crossed seeds from pollination of 'Maruba Kaido' with 'M.9', which had been cultivated at the Morioka Branch of the Fruit Tree Research Station (currently the Apple Research Center, the National Institute of Fruit Tree Science), and after seeding the following year and raising at a nursery, the seedlings were selected based on a bark/wood ratio of the roots of more than 60% and a propagability by hardwood cuttings of more than 50%, and a noteworthy individual was selected in 1984.

The breeders asexually reproduced the individual from hardwood cuttings, as a strain number Apple Rootstock 'Morioka No. 7', and from 1985 began the local adaptability test of the rootstock at 12 testing centers in apple producing regions such as Hokkaido, Aomori prefecture, Akita prefecture, Yamagata prefecture and Nagano prefecture.

The excellent results were obtained from the trials, on such characteristics as hardwood cutting reproduction ability as well as dwarfing capability and disease/insect resistance, while its homogeneity and stability were also confirmed, as was its distinctness from the parent variety 'Maruba Kaido', 'M.9' and the control variety 'M.26'; in 1996 the Apple Rootstock 'Morioka No. 7' was named as the new variety 'JM7'. The genus and species of this tree is *Malus prunifolia* var. '*Ringo*'×*Malus pumila* var. 'Paradisiaca'.

SUMMARY OF THE VARIETY

The new variety of apple tree has moderate vigor, and exhibits "spreading". The roots have tolerance to flood/waterlogged soil, comparable with that of 'Maruba Kaido'. The survival rate was as high as 95%, greatly facilitating reproduction from hardwood cuttings. The current shoot resulting from the hardwood cuttings was upright and exhibited satisfactory growth, reaching a size which was usable for a rootstock in one season. Resistance to major diseases included crown rot and Alternaria blotch resistance. It also exhibited resistance to the major parasite, wooly apple aphid. No susceptibility was exhibited for the top-working disease virus, ASPV (apple stem pitting virus), but it was susceptible to ACLSV (apple chlorotic leaf spot virus).

The ripening period for the fruit is in early to middle October. The fruit averages about 27 g and is quite small. The fruit skin color is yellow. It has a high sugar content, (about Brix 16.6%) and is extremely acidic (1.19 g/100 ml titratable acidity) with an astringent taste, making it unsuitable for eating consumption.

When the variety is used as a rootstock it exhibits dwarfing ability comparative to 'M.9 EMLA'. Its grafting compatibility with 'Fuji' (unpatented) is "fair" to "good", and it exhibits overgrowth of the rootstock such that the unions between scion and rootstock in 17-year trees of 'Fuji' on 'JM7' show stock swelling. The average trunk diameter of 'Fuji' above the graft union is 15.2 cm whereas the average trunk diameter of 'JM7' below the union is 26.3 cm. Comparing both diameters, the rootstock showed 73% more overgrowth than the scion.

The production efficiency as measured for a 'Fuji' scion grafted on the rootstock is higher than for 'M.9 EMLA' or 'M.26 EMLA', giving an abundant yield, as shown in the following data.

In 1985, 2-year 'Fuji' trees on 'JM7' were planted in an orchard to confirm their field performance. Trees on 'M.9 EMLA' and 'M.26EMLA' served as controls. Trunk diameter and tree height were measured, and fruit yields collected each year. Yield efficiency is used as a reliable predictor of productivity/unit area. Cumulative yield efficiency, as shown in the following table, is calculated by cumulative yield per tree (Kg)/trunk cross-sectional area ($cm^2$).

TABLE

Tree size, yield efficiency, and selected fruit traits for 13-year-old 'Fuji', with apple rootstock clones.

| Rootstock | Trunk girth (cm) | Cumulative yield/tree (kg) | Cumulative yield efficiency ($kg/cm^2$ TCA | Mean fruit weight[2] (g) | Soluble solids[2] (%) | Flesh firmness[2] (kg) |
|---|---|---|---|---|---|---|
| 'JM 7' | 41.5 | 332 | 2.42 | 282 | 16.1 | 16.0 |
| 'M.9 EMLA' | 44.7 | 251 | 1.58 | 257 | 14.5 | 15.8 |
| 'M.26 EMLA' | 57.0 | 311 | 1.20 | 264 | 14.3 | 15.5 |
| LSD 5% | 3.6 | 44 | 0.41 | 23 | 0.7 | 0.3 |

[2]Mean of 1993–1995 at Morioka City, Japan

The weight of the fruits produced using this variety as the rootstock is about the same as using the control rootstocks 'M.9 EMLA' and 'M.26 EMLA', but the uniformity is somewhat superior. High quality fruit is produced, with a higher hardness and sugar content than the control stocks, and color of "fair" to "good".

The new variety is distinguished from the control stock 'M.26' by having fruit which has a later ripening period, smaller size and stronger acidity, being capable of reproduction from hardwood cuttings, and being resistant to wooly apple aphid. The new variety is also distinguished from the pollen parent 'M.9' by having fruit which has a later ripening period, smaller size and stronger acidity, being capable of reproduction from hardwood cuttings, and being resistant to wooly apple aphid. Also, the new variety is distinguished from the seed parent 'Maruba Kaido' by having a thick and upright current shoot, and by having dwarfing ability when utilized as a rootstock.

The color values presented are herein from The Royal Horticultural Society (R.H.S.) Colour Chart.

DESCRIPTION OF THE VARIETY

Figure 1:
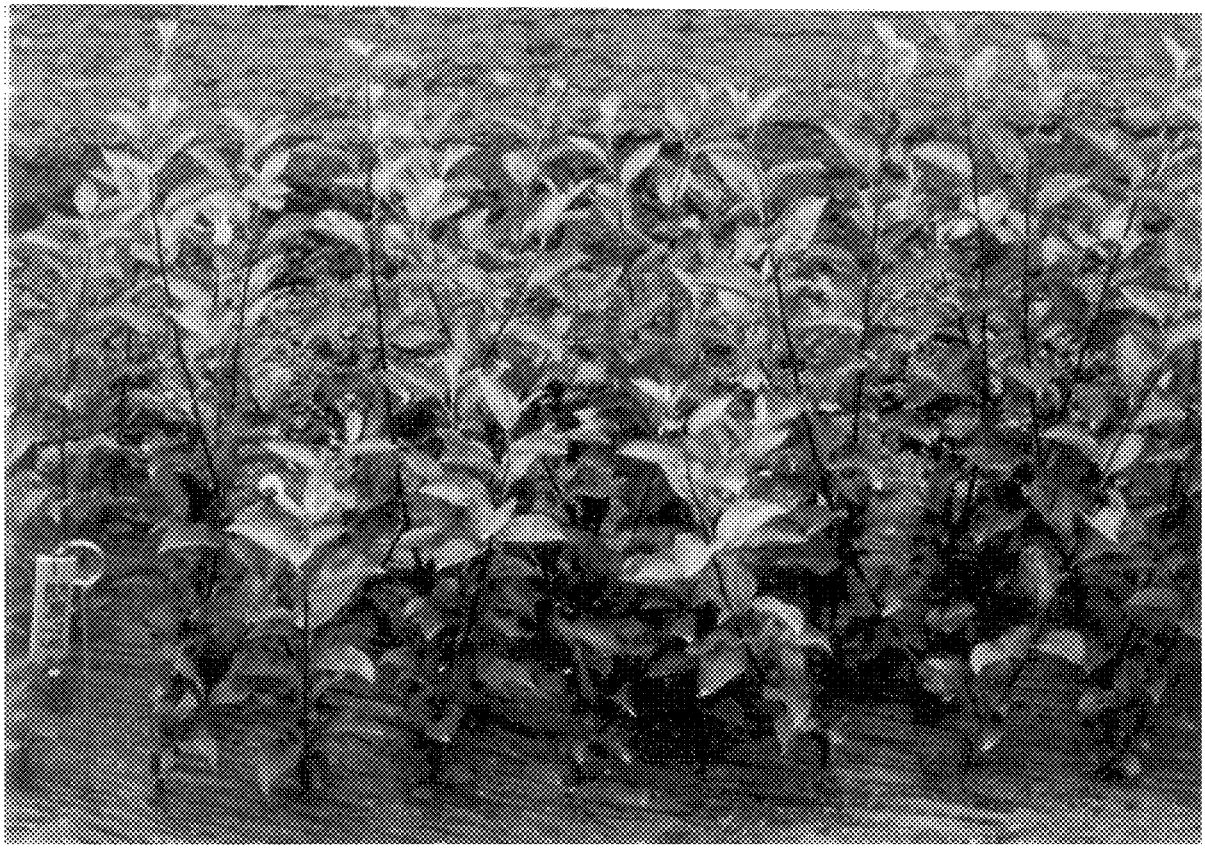
FIG. 1 is a photograph showing the state of the growth and development of the new variety of apple trees after hardwood cuttings.
Figure 2:
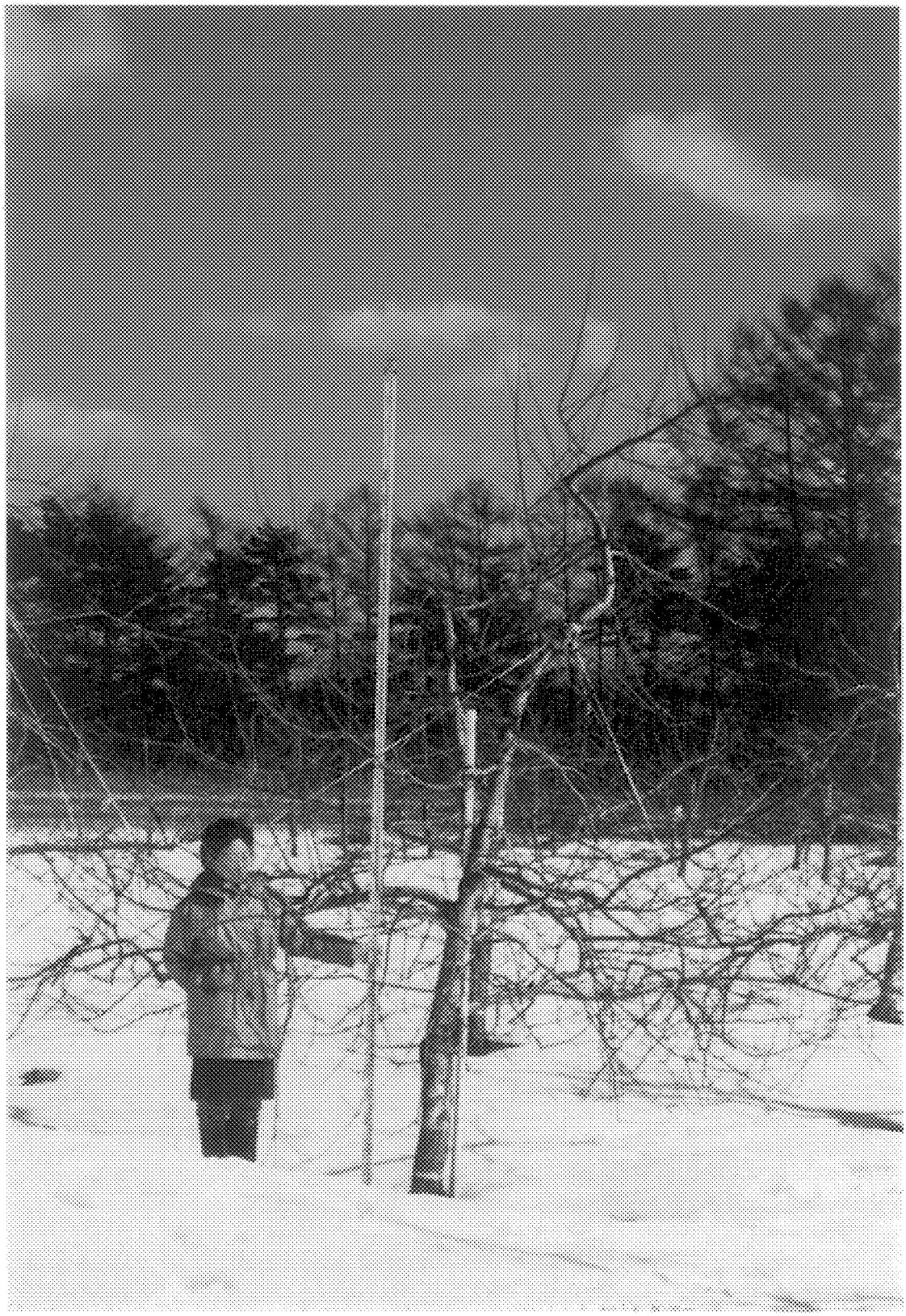
FIG. 2 is a photograph of a thirteen year old 'Fuji' apple tree grafted onto the 'JM7' rootstock variety, which is beneath the snow line.
Figure 3:
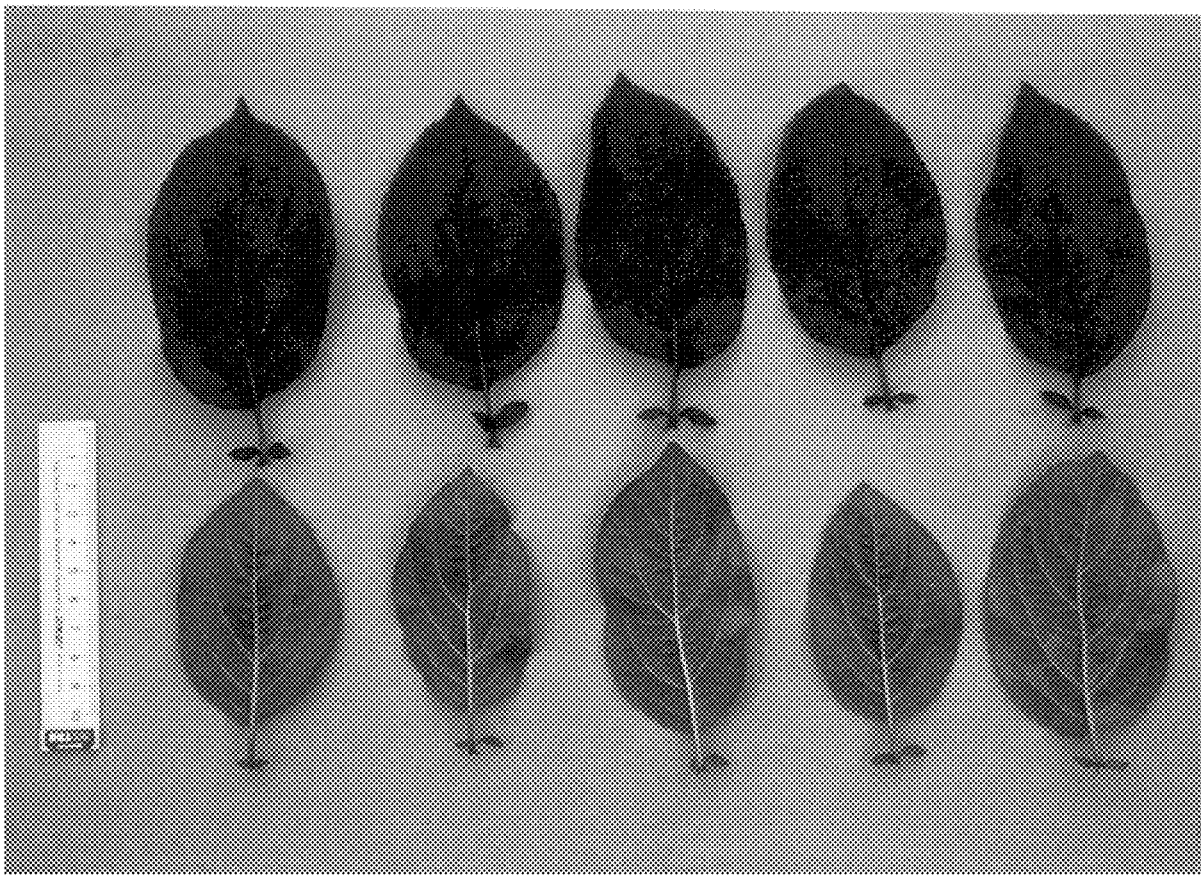
FIG. 3 is a photograph of adult leaves of the new variety of apple tree.
Figure 4:
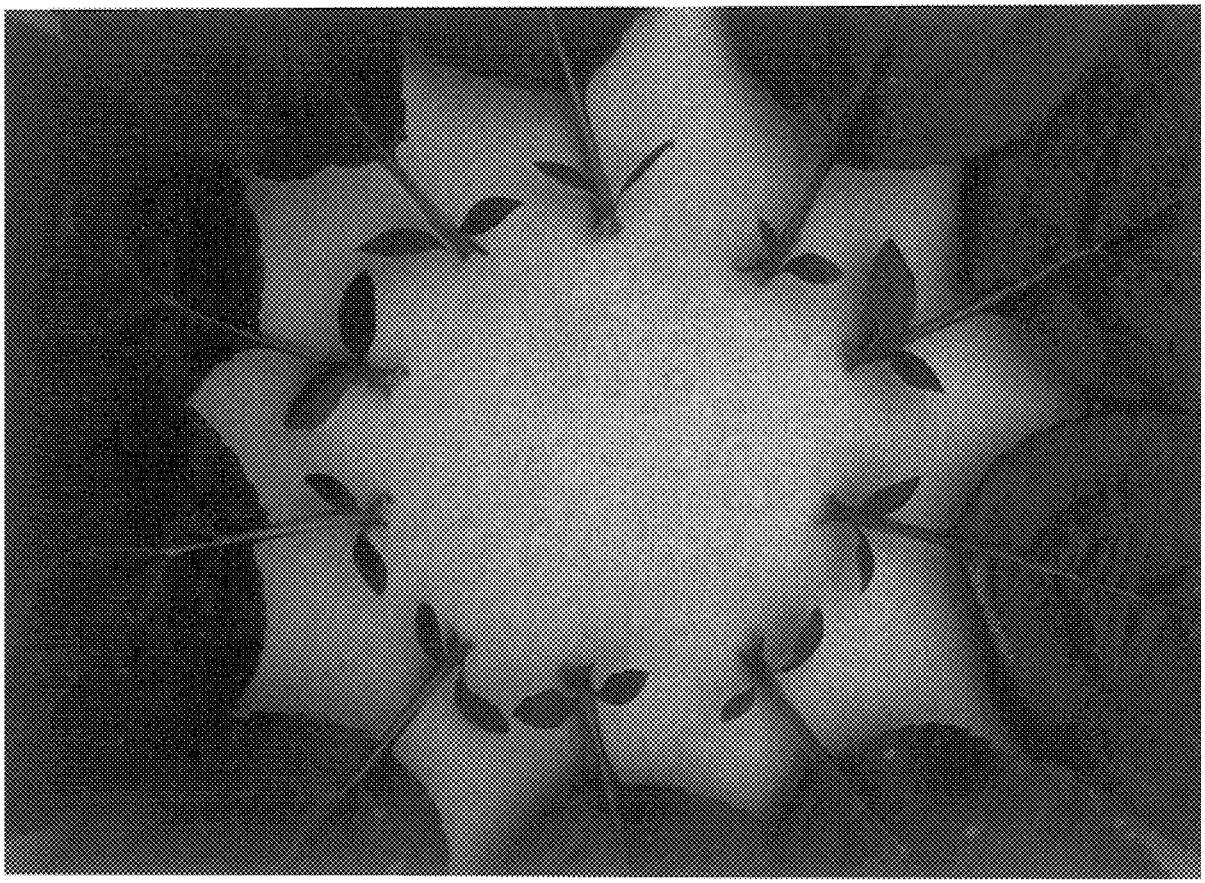
FIG. 4 is a photograph of petioles and stipules of the new variety of apple tree.
Figure 5:
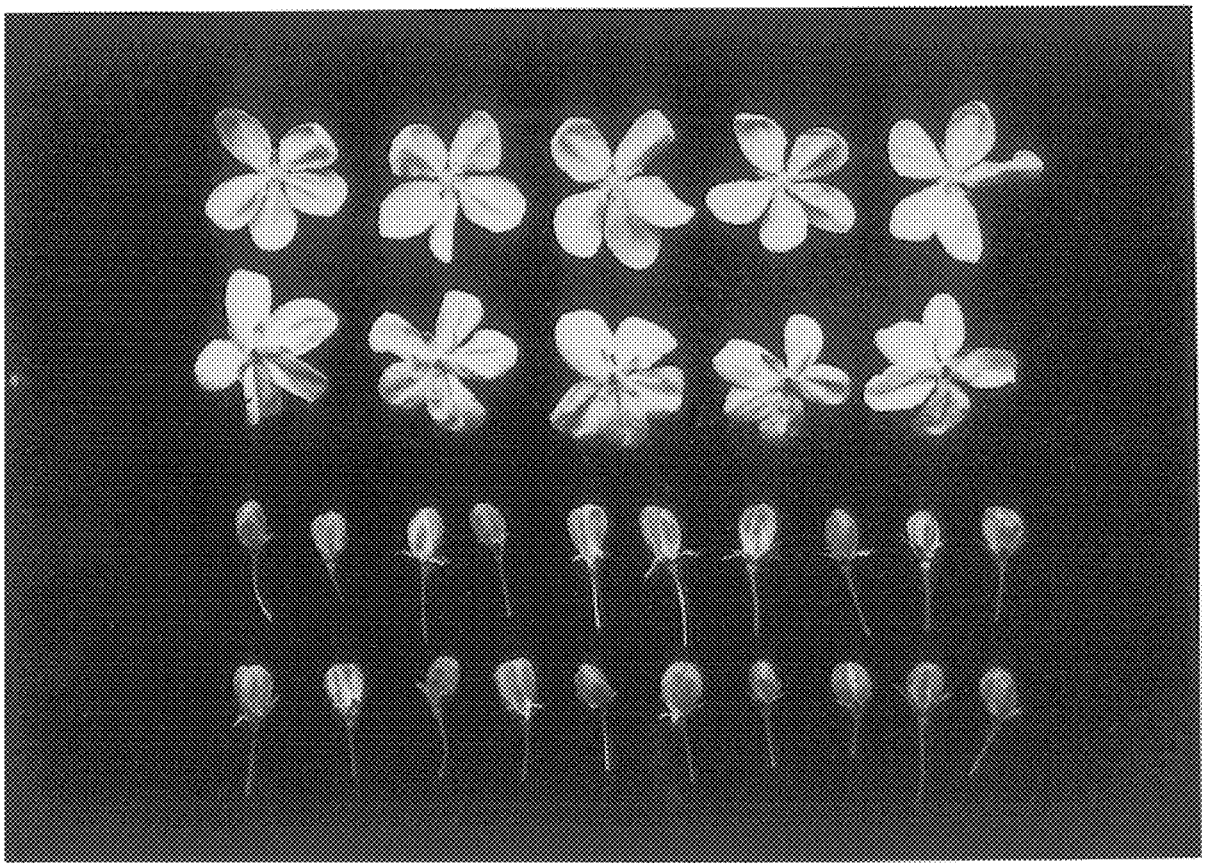
FIG. 5 is a photograph of opened flowers (the top rank and the second rank) and unopened flowers (the third rank and the fourth rank) of the new variety of apple tree)
Figure 6:
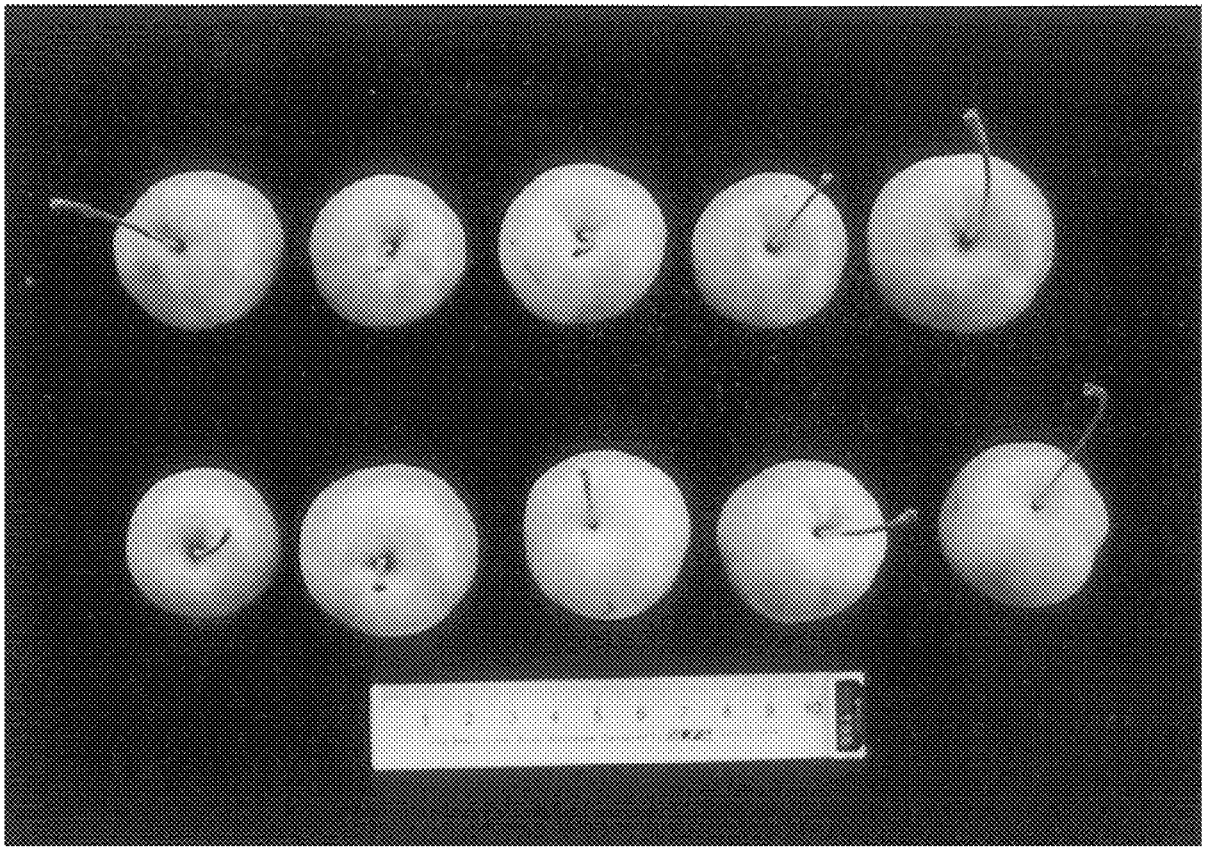
FIG. 6 is a photograph of views of the stem end of fruit of the new variety of apple tree, as it approaches maturity.
Figure 7:
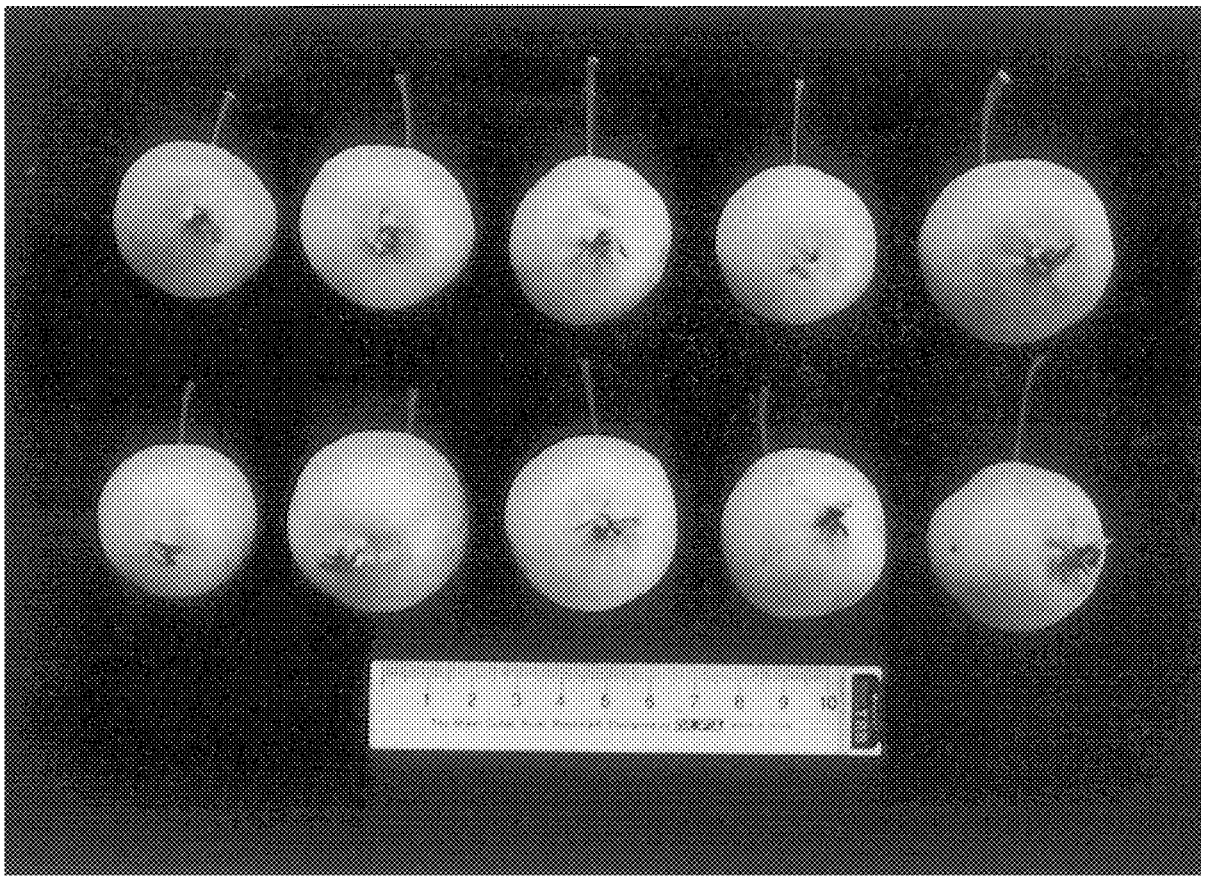
FIG. 7 is a photograph of views at the blossom end of fruit of the new variety of apple tree, as it approaches maturity.
Figure 8:
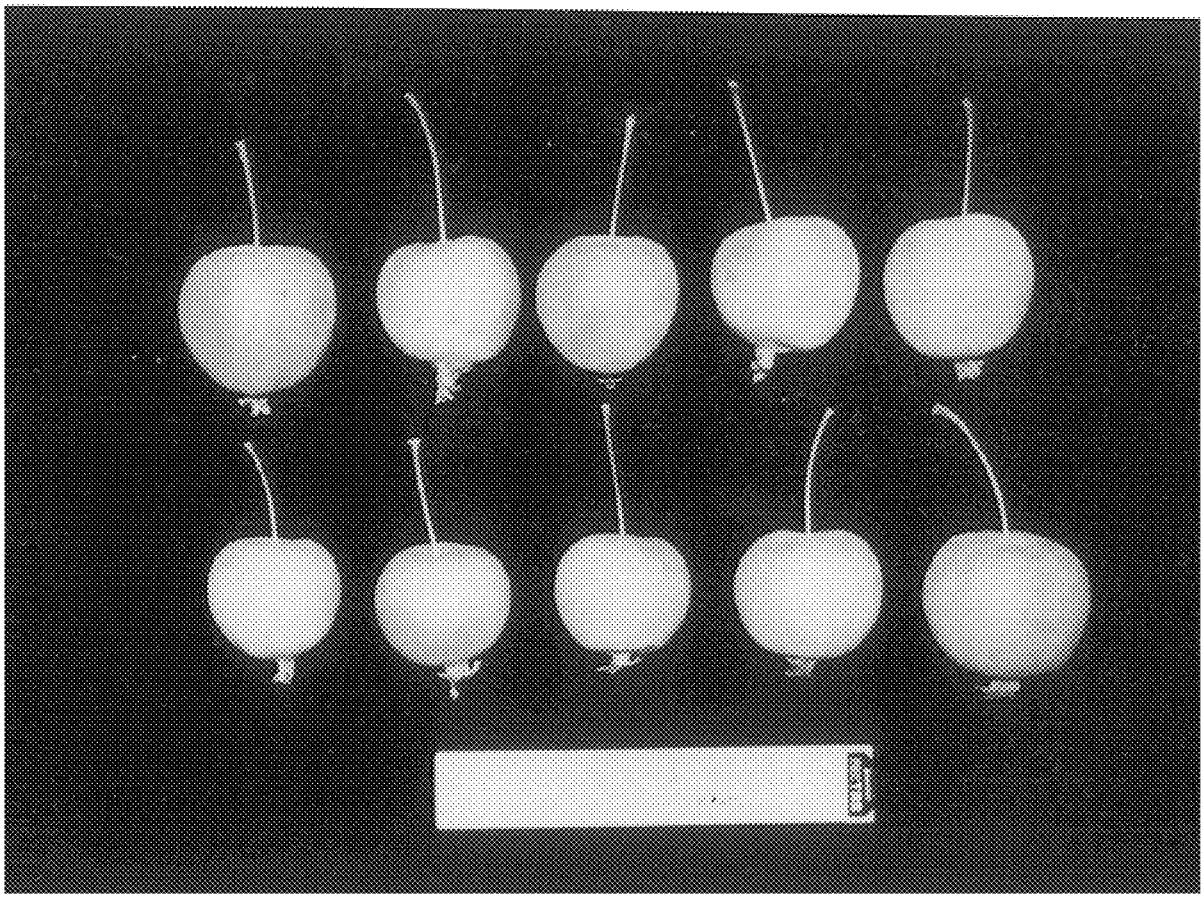
FIG. 8 is a photograph of side views of the fruit of the new variety of apple tree.
Figure 9:
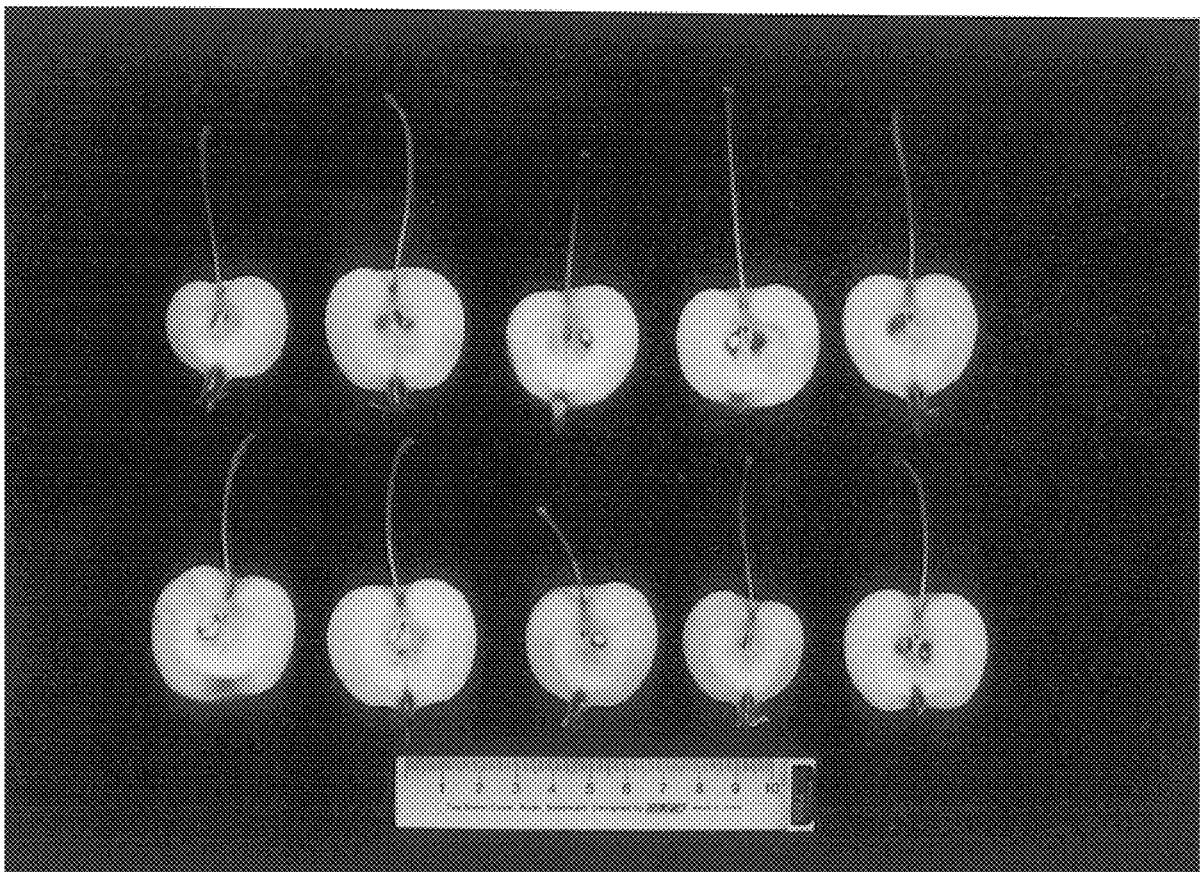
FIG. 9 is a photograph of longitudinal-section views of the fruit of the new variety of apple tree.
Figure 10:
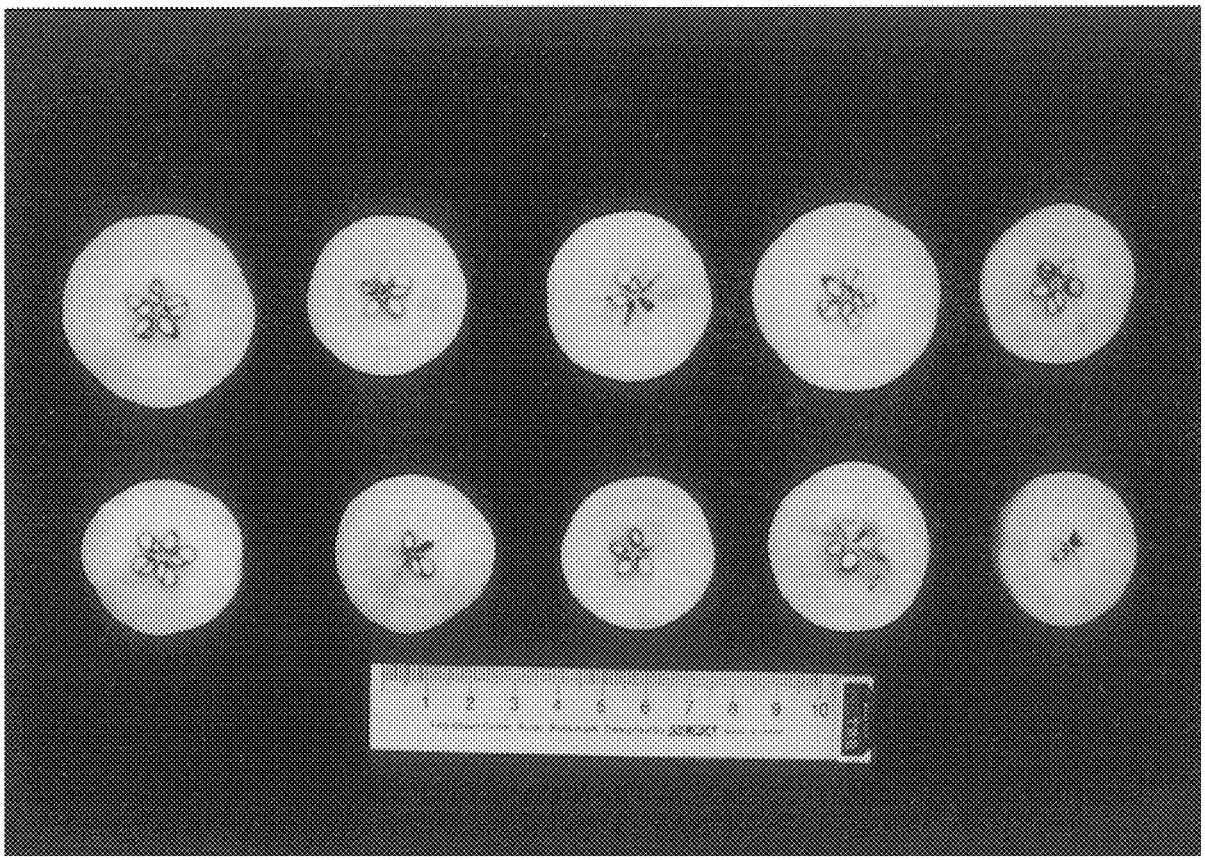
FIG. 10 is a photograph of cross-sectional views of the fruit of the new variety of apple tree.

The characteristics of the new and distinct variety of apple tree 'JM7' are as follows:

Tree:

*Habit of branches.*—Spreading.
*Size.*—Small.
*Vigor.*—Medium.
*Thickness* (*one-year-old shoot*).—Stout (average diameter 6.4 mm).
*Length of internode* (*one-year-old shoot*).—Medium (about 2.9 cm).
*Size of lenticels* (*one-year-old shoot*).—Large.
*Number of lenticels* (*one-year-old shoot*).—Medium.
*Pubescence of shoot.*—Absent or very weak.
*Predominance of bearing.*—Bears heavily on spurs.
*Bearing of axillary flower bud.*—There are few axillary flower buds.
*Bark.*—R.H.S. Greyed — Red 178A.

Leaf:

*Shape of leaf blade.*—Ovate.
*Serrations of leaf edge.*—Crenated.
*Size of leaf* (*length*).—Medium (length about 9.7 cm. wide about 5.7 cm).
*Color of leaf* (*upper surface*).—R.H.S. Green 135A.
*Color of leaf* (*lower surface*).—R.H.S. Green 138B.
*Pubescence of leaf.*—Sparse.
*Shape of stipules.*—Rounded.
*Length of stipules.*—Long (average length of individual stipule is 12.7 mm for mature leaf).
*Length of petiole.*—Short (average 17.1 mm for mature leaf).
*Thickness of petiole.*—Stout.

Flowers:

*Number of flowers* (*per cluster*).—Medium (average 5.7).
*Size* (*open flower*).—Large (average diameter 5.4 cm).
*Color* (*unopened flower*).—Deep pink.

*Color* (*opened flower*).—R.H.S. Red-Purple 62D.
*Shape of petal.*—Ovoid.
*Number of petals.*—Medium (5).
*Number of stamens.*—Medium.
*Color of anthers.*—Bright yellow.
*Amount of pollen.*—Much.
*Fragrance.*—Typical of apple.

Fruit:

*Shape.*—Conical, whereas that of 'M.26' and 'M.9' is oblate.
*Crowning at eye end.*—Absent.
*Aperture of eye.*—Closed.
*Depth of basin* (*eye end*).—Shallow.
*Breadth of basin* (*eye end*).—Narrow.
*Depth of stalk cavity.*—Shallow.
*Breadth of stalk cavity.*—Medium.
*Size.*—Very small (about 27 g, average diameter 2.4 cm, average circumference 7.4 cm), smaller than 'M.26' (about 113 g) and 'M.9' (about 43 g).
*Color.*—Ground color is R.H.S. yellow 8B.
*Type of over color of skin.*—No distinctive over color or stripe in mature fruit.
*Amount of blush of skin.*—80–90% of total surface of fruit.
*Position of russet.*—Around cavity.
*Amount of russet.*—Absent or very slight.
*Raised russet lenticels.*—Present, whereas absent in 'M.9'.
*Size of lenticels.*—Small.
*Number of lenticels.*—Many.
*Silvery mottle of skin* (*scarfskin*).—Absent.
*Shininess of skin.*—Strong.
*Greasiness of skin.*—Medium.
*Bloom of skin.*—Absent.
*Cracking tendency of skin.*—Absent.
*Surface texture of skin.*—Moderate.
*Length of stalk.*—Long (about 4.9 cm), longer than 'M.26' and 'M.9'.
*Thickness of stalk.*—Slender, slightly more slender than 'M.9'.
*Distinct swelling at end of stalk.*—Absent.
*Shape of core.*—Conical.
*Size of core.*—Large (5 core cells).
*Color of flesh.*—Yellow (R.H.S. Yellow 4D), that of 'M.9' is white.
*Easy bruising of flesh.*—Medium.
*Browning of flesh.*—Strong.
*Firmness of flesh.*—Medium.
*Texture of flesh.*—Coarse.
*Water core.*—Absent or weak.
*Sweetness of flesh.*—Strong (about Brix 16.6%) stronger than 'M.9' (about Brix 8.4%).
*Acidity of flesh.*—Strong (about 1.19%), stronger than 'M.9'.
*Astringency of flesh.*—Present.
*Flavor of flesh.*—Weak.
*Juiciness of flesh.*—Medium.

Seed:

*Number of fully developed seeds.*—Medium (average 5.9).
*Shape.*—Obovoid.
*Size.*—Small.
*Color.*—R.H.S. Greyed-Orange 175B.

Physiological and ecological characteristics:

*Date of germination.*—Medium (April 11$^{th}$ at Morioka City, Japan).
*Season of flowering.*—Late (Around May 20$^{th}$, at Morioka City, Japan).
*Season of leaf fall.*—Medium.
*Time fruit are ripe for eating.*—Medium (Around October 6 to 15$^{th}$, at Morioka City, Japan, later than 'M.9' (around September 17$^{th}$).
*Precocity.*—Precocious. 'Fuji' trees grafted on 'JM7' began fruiting in 4$^{th}$ year, just as for 'Fuji' grafted on 'M.9 EMLA', and 2 years earlier than for 'Fuji' grafted on 'Maruba Kaido' (*Malus prunifolia*).
*Self-fruitfulness.*—Medium.
*Early dropping of fruit.*—Medium.
*Preharvest dropping of fruit.*—Medium.
*Physiological disorder of fruit.*—Few.
*Keeping quality of fruit* (*normal storage*).—Short (about 6 days).
*Keeping quality of fruit* (*cold storage*).—Short (about 30 days).
*Occurrence of heat rot* (*core rot*).—Absent or weak.
*Resistance to alternaria blotch.*—Resistant, same as 'M.9'.
*Resistance to powdery mildew.*—Susceptible.
*Resistance to rough bark disorder.*—Resistant.
*Resistance to aphid.*—Susceptible.
*Resistance to wooly apple aphid.*—Resistant, whereas 'M.26' and 'M.9' are susceptible.
*Grafting.*—Easy.
*Rooted cuttings.*—Easy, whereas hard in 'M.26' and 'M.9'.
*Vegetative propagation.*—Easy, easier than 'M.26' and 'M.9'.
*Habit of tree vigor after grafting.*—Moderate, and shows a dwarfing ability as a rootstock.
*Development of roots.*—Medium.
*Tolerance to flood/water-logged soil.*—Strong, stronger than 'M.26' and 'M.9'. Nursery stocks planted in plastic pots and treated with flooding for 63 days exhibited ratio of defoliation (as measured by number of defoliated leaves during that period) was 19%.
*Drought resistance.*—Medium.
*Culture.*—Since the new variety is susceptible to the top-working disease virus ACLSV, it succumbs to the disease when grafted with a carrier scion. Therefore, it is necessary to use scions free from ACLSV. For planting of nursery stock, support posts are required to prevent lodging, as for dwarfed trees of 'M.9' and 'M.26'.

As a dwarfing rootstock, the instant variety is compatible with 'Fuji', 'Orin', 'Tsugaru', 'Sansa', 'Jonagold', 'Senshu', etc., and it is not known what varieties are incompatible with the instant variety. Regarding percent of dwarfing capability over plants on their own roots, the scion trunk diameter in 15-year trees of 'Fuji' on 'JM7' showed 88%, and regarding percent dwarfing capability compared with 'M.9EMLA' and 'M.26EMLA', that of 'JM7' is 70% over plants on roots of 'M.9EMLA' and 'M.26EMLA'. 'JM7' has dwarfing capability, even if it is used as an interstem.

When varieties of 'Fuji', 'Orin', 'Tsugaru', 'Sansa', 'Jonagold', 'Senshu', etc., were grafted on 'JM7' rootstocks and grown, no occurrence of particular physiological disorder has been observed to date.

Because the new variety has superior qualities as an apple dwarfing rootstock, it is suitable for use in all cultivation zones for apples, and it is believed that it will rapidly come into wide use in place of the currently used rootstocks, 'M.9' and 'M.26'.

We claim:

1. A new and distinct variety of apple tree, substantially as illustrated and described.

* * * * *